(12) United States Patent
Vallittu et al.

(10) Patent No.: US 6,197,410 B1
(45) Date of Patent: Mar. 6, 2001

(54) PREPREG

(75) Inventors: Pekka Vallittu, Kuusisto; Antti Yli-Urpo, Littoinen; Ilkka Kangasniemi, Turku, all of (FI)

(73) Assignee: Stick Tech Oy, Turku (FI)

( * ) Notice: Subject to any disclaimer, the term of this patent is extended or adjusted under 35 U.S.C. 154(b) by 0 days.

(21) Appl. No.: 09/251,473

(22) Filed: Feb. 17, 1999

Related U.S. Application Data (63) Continuation of application No. PCT/FI99/00120, filed on Feb. 15, 1999.

(30) Foreign Application Priority Data

Mar. 9, 1998 (FI) ........................................ 980528

(51) Int. Cl.⁷ ........................................ C08K 3/00
(52) U.S. Cl. ........................ 428/292.1; 524/494; 524/495; 524/496
(58) Field of Search ........................ 428/292.1; 524/494, 524/495, 496

(56) References Cited

U.S. PATENT DOCUMENTS

| | | | |
|---|---|---|---|
| 4,264,655 | 4/1981 | Brook | 427/381 |
| 5,597,631 | 1/1997 | Furumoto et al. | 428/364 |
| 5,846,640 | 12/1998 | Vallitu | 428/306.6 |

*Primary Examiner*—Edward J. Cain
(74) *Attorney, Agent, or Firm*—James C. Lydon (57) ABSTRACT

This invention relates to a shapable prepreg comprising fibers and a polymeric matrix. The polymeric matrix is a multiphase matrix comprising a first matrix component consisting of a monomer or a dendrimer, and a second matrix component consisting of high molecular weight organic molecules, said second matrix component forming a sticky membrane of the prepreg with an interpenetrating polymer network (IPN) bonding to the first matrix component. Preferably, the prepreg further comprises a third matrix component consisting of high molecular weight organic molecules, said third component being distributed between the fibers.

21 Claims, 4 Drawing Sheets

PREPREG

This application is a continuation of PCT/FI99/00120 Feb. 15, 1999.

FIELD OF THE INVENTION

The present invention relates to a novel prepreg, a method for the preparation of the prepreg and a method for packing the prepreg. The invention relates further to a fibre-reinforced composite based on the use of said prepreg, and the use of said fibre-reinforced composite.

BACKGROUND OF THE INVENTION

The publications and other materials used herein to illuminate the background of the invention, and in particular, cases to provide additional details respecting the practice, are incorporated by reference. Many daily goods and special goods resemble dental and medical devices, made from polymers, in the fact that they are prone to fracture due to mechanical conditions of human body or use. In dentistry, it is well documented that removable dentures can fracture after the denture has been worn for some years, (1–3). In orthopedics, bone cements have been proved to be a weak link between e.g. joint implant and bone (4,5). During last few decades, fibre-reinforced composite (FRC) materials instead of unreinforced polymers have been tested as materials more suitable to the dental and medical applications. Attempts have been made to develop a polymer fibre composite material which fullfills the biological requirements and requirements of clinical dentistry and orthopedic surgery for such fibre-reinforced composite material. Recently, an invention of polymer preimpregnated fibre material (prepreg) was introduced for dental and some medical applications (6). Said prepreg made it possible to use fibre composite materials together with multiphase acrylic resins which have relatively high viscosity prior polymerization. The multiphase acrylic polymer are made from prepolymerized powder particles, such as polymethylmethacrylate (PMMA) and monomer liquid, such as methyl methacrylate (MMA) and ethyleneglycol dimethacrylate (EGDMA) (7). Multiphase acrylic resins were used in dental devices and in orthopedic bone cements (7,5). The use of said prepreg resulted in a well impregnated fibre composite with good mechanical properties. Since then, clinical studies have shown that the use of such polymer preimpregnated prepreg eliminates recurrent fractures of acrylic resin removable dentures (8).

Although the above prepreg has resolved the problem to reinforce multiphase acrylic resins of removable dentures with fibres, said prepreg has not resolved certain other problems relating to the use of fibre-reinforced composite materials in dentistry. In many dental applications polymers are made from monomer liquid systems only, instead of powder-liquid mixtures as described earlier. These systems are typically made from dimethacrylate resins, such as BISGMA and triethyleneglycoldimethacrylate (TEGDMA) and polymerized by activation of an initiator by visible light radiation (9). The viscosity of such monomer systems were regulated by changing the ratio of monomers and this resulted in such monomer system which could be used in preimpregnation of fibres with monomers. Such products (Vectris, Vivadent/Ivoclar, Liechtenstein; FibreKor, Jeneric/Pentron, USA) are on the marked. Due to quite difficult handling of dimethacrylate monomer preimpregnated fibres, extensive number of equipment was needed to use these products in dental laboratory. The main problem in this respect with the aforementioned monomer preimpregnation method was that fibres frayed to undesired regions in dentition when the prepregs were placed on teeth. In addition, the processing of the monomer preimpregnated fibres with hand laminating technique sensitize the dental personel to allergy by monomers.

Another great disadvantage of using such monomer preimpregnated fibre systems in dental bridges was that conventional type of tooth preparation was needed. This means that a great amount of dental enamel and dentine was ground in order to get space for the restorative material. This kind of restorative dentistry could be called as "invasive prosthetic dentistry" and one complication of this kind of treatment was hypersensitivity of tooth or necrosis of the pulp tissue. Need for the tooth preparation was minor with so called "resin-bonded-bridges" or "Maryland bridges", which were made from cast metal alloy and luted to tooth with resin cements (10, 11). A disadvantage of this kind of restoration was recurrent debonding of the restoration and relatively high price of the restoration because of complicated laboratory technique (10, 11).

Carbon/graphite and glass fibre-epoxy composites have been developed for use in root canal posts (12, 13). Root canal posts posts were used to restore tooth for an artificial crown. Traditionally, root canal posts were made from individually cast metal alloys or from metal screws. Fibre-epoxy root canal posts might have potential to replace traditionally used materials. However, one shortcoming of the fibre-epoxy composite posts in dental application have been reported. This is inadequate adhesion between resin luting cement and the fibre-epoxy composite post which lead to loosening of the post after some period of time (14). This was due to the highly cross-linked thermosetting polymer structure of the epoxy which did not allow formation of the interpenetrating polymer network (IPN) bonding or radical polymerization bonding (15).

In summary, the problems which relate to the state-of-the-art methods in the field are:

1) Prepregs made from monomer systems were difficult to handle by dentists and dental technicians because preimpregnation monomer did not sufficiently bind the fibres together.

2) Handling of monomer preimpregnated prepregs sensitize dental personel to monomers by skin contact to the prepreg.

3) The treatment with conventional dental bridges required tooth preparation and can be defined as "invasive prosthetic dentistry".

4) By using less invasive prosthodontic techniques, such as resin-bonded-bridges, recurrent debonding of the luting cement from the metal frame of the bridge was a problem.

5) By using currently available fibre-epoxy composite endodontic posts, loosening of the post from the root canal was a problem.

In addition, an unsolved problem with all polymers used in dentistry was the polymerization contraction of the resin (9). This lead to poorly fitting restoration and dentures and caused marginal leakage of restoration.

The use of a semisolid encapsulated fibre roving prepreg was described in the U.S. Pat. No. 4,264,655 (16). In that prepreg, the fibres were preimpregnated with heat-curing thermosetting resin and thereafter covered with a membrane of thermoplastic resin. It was emphasized that the thermoplastic membrane remained distinct part from the thermosetting resin and no bonding was obtained, or desired, between the polymer phases. In addition, thermoplastic membrane was such that it eliminated interstrand adhesion of prepregs.

Another U.S. Patent (U.S. Pat. No. 5,597,631) (17) described a prepreg which had a thermoplastic film coverage. The purpose of the film coverage was to increase the strength of the fibre-reinforced composite made from the prepreg by means of high strength and high modulus of the polymer used in the film coverage. However, this film, although it was bonded to the fibre-rich part of the thermoplastic prepreg, the film was not able to cause interstrand adhesion of the prepregs because the prepreg was thermoplastic in type, which is a desired property for the prepreg used in dentistry.

OBJECT AND SUMMARY OF THE INVENTION

Many daily goods and different equipments shall meet the requirements imposed by clinical dentistry and dental technology on a prepreg made from fibres and monomer systemsn useful in dentistry. The main requirements are the following:

1) the composition of an unpolymerized (i.e. non-cured) resinous phase of the prepreg must be so cohesive that the resinous phase keeps sufficiently the shape of the prepreg although it is in unpolymerized form, 2) the prepreg should be plastic enough at room's and body's temperature, 3) the prepreg should be totally impregnated with the resinous material, 4) the prepreg should be polymerized e.g. by autopolymerization, heat-polymerization, microwave-polymerization or by light-polymerization, 5) the composite material made from the prepreg should adhere strongly to the resinous materials used in dentistry and medicine (e.g. resinous luting cements of BISGMA and TEGDMA), 6) the polymerization contraction of the composite should be as low as possible, 7) by pressing prepregs together prior to polymerization they should bind sufficiently together (interstrand adhesion), and 8) the package of the prepreg should enable the shaping and polymerization of the prepreg and avoid skin contact of monomers to the hands of dental personel.

One object of the invention is a prepreg fulfilling the aforementioned requirements 1) to 8).

Another object of the invention is the use of said prepreg in the manufacture of fibre-reinforced composites. Said composites are suitable for use in any technical field, paticularly in dental or medical field.

Thus, according to one aspect, the invention concerns a shapable prepreg comprising fibres and a polymeric matrix, characterized in that the polymeric matrix is a multiphase matrix comprising a first matrix component consisting of a monomer or a dendrimer, and a second matrix component consisting of high molecular weight organic molecules, said second matrix component forming a sticky membrane of the prepreg with an interpenetrating polymer network (IPN) bonding to the first matrix component.

According to another aspect, the invention concerns a prepreg comprising fibers and a polymer distributed between the fibres. According to the invention, the polymer is epsilon-caprolactone/PLA, epsilon-caprolactone, D- and L-lactide, PLA-, PGA-molecules, polyorthoesters, or an other bioactive, biocompatible polymers having molecular weight in the range 5,000 to 400,000.

According to a third aspect, the invention concerns a prepreg comprising fibers and a polymer distributed between fibres, wherein between the fibres are further distributed additives such as Si, Ca, P, Ba, Mg, K, Na, Ti, F, oxides or other coumpounds of said elements, colour pigments, inert ceramics; hydroxyapatite (HA) or other Ca phosphates, $Al_2O_3$, $ZrO_2$, xerogels, bioactive glasses or functionally bioactive or therapeutically active molecules, antigens, antibiotics, desinfectants, radio opaque materials, organic acids such as maleic acid, polyacrylic acid, or the like.

According to a fourth aspect, the invention concerns a process for the preparation of the prepreg wherein fibres are wetted in a monomer or a dendrimer, and that the product so obtained optionally is further wetted in a solution of high molecular weight organic molecules.

According to a fifth aspect, the invention concerns a package of the prepreg, characterized in that it comprises the prepreg surrounded by a metal foil bottom and one or two layers of plastic sheet coverage, the closest sheet to the prepreg being a clear translucent sheet and the outermost sheet being a translucent sheet, treated so as to not essentially pass the light for curing.

According to the further aspects, the invention concerns a composite based on said prepreg as well as the uses of said composite.

DETAILED DESCRIPTION OF THE INVENTION

Figure 1A:
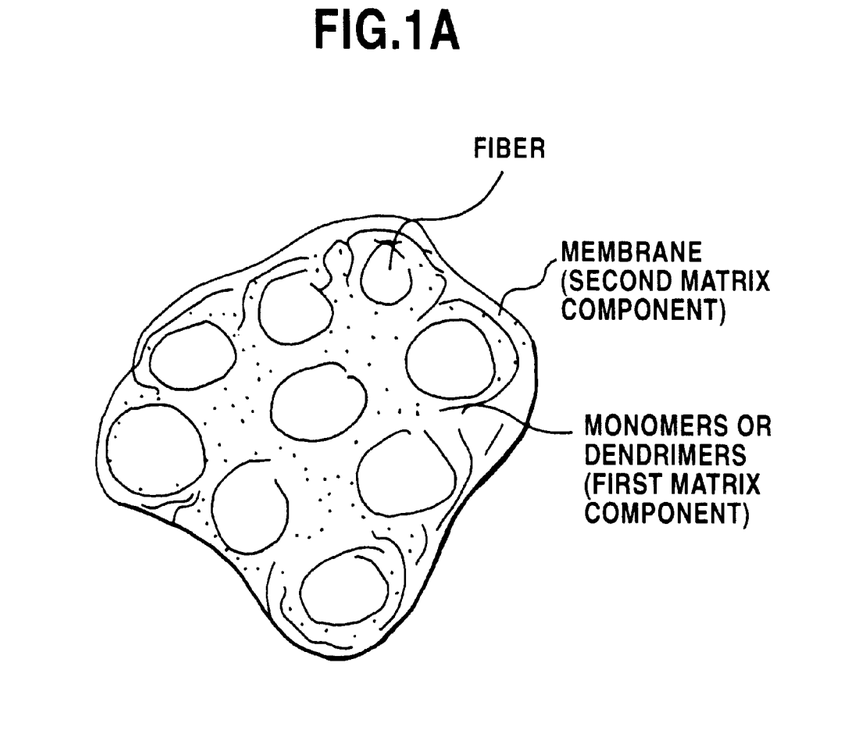
FIGS. 1A and 1B show two different prepregs according to this invention.
Figure 1B:
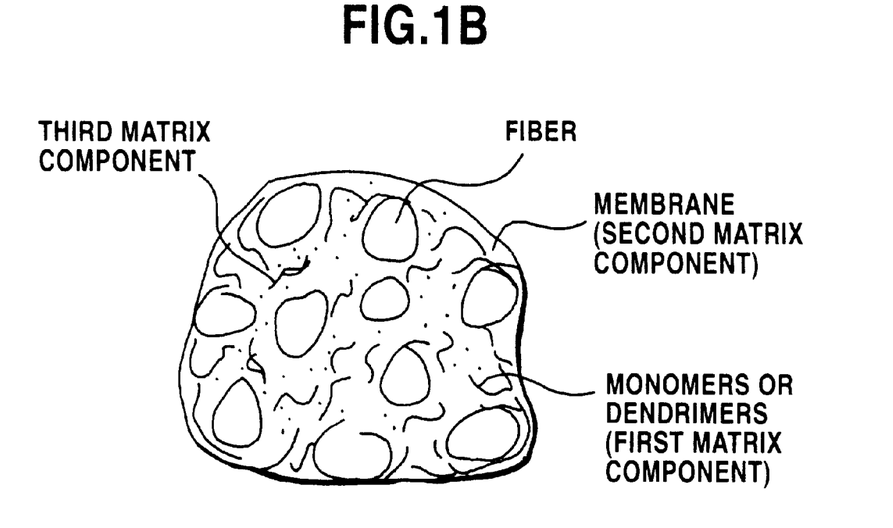

FIG. 1A shows a prepreg according to the invention, where the prepreg consists of fibres, a first matrix component and a second matrix component. According to a preferred embodiment, the prepreg further comprises a third matrix component (see FIG. 1B) consisting of high molecular weight organic molecules, e.g. of thermoplastics, said third matrix component being distributed between the fibres.

The first matrix component and the third matrix component form a gel. The prepreg preferably contains ingredients necessary to initiate the polymerization at a desired point of time. All the necessary ingredients can be included, except for the case where the curing process is based on autopolymerization. In this case, the addition of at least one of the necessary ingredients should be postponed until the polymerization (curing) is desired.

According to another preferable embodiment, the prepreg contains additives such as bioactive or inert filler materials, colour pigments or therapeutical materials.

Altough the membrane covering the fibers can be made just by polymerization of the monomer on the surface layer of the prepreg, it is preferable to create the membrane by dipping the preform in a separate solution of a polymer.

A preferable process for the preparation of the prepreg according to this invention comprises the following steps:

a) impregnating the fibres with a liquid containing high-molecular weight organic molecules, such as PMMA molecues with molecular weight of 190,000 to 900,000 or epsilon-caprolactone/PLA, epsilon caprolactone, D- and L-lactide, PLA- or PGA-molecules or other thermoplastic biocompatible polymer molecules having a molecular weght in the range 5,000 to 400,000 in a rapidly evaporating organic solvent, such as tetrahydrofuran (THF), acetone, or the like; said liquid optionally containing additives such as different inert or bioactive fillers containing elements such as Si, Ca, P, Ba, Mg, K, Ti, F, oxides or other compounds of said elements, colour pigments, inert ceramics, hydroxy apatite (HA) or other Ca-phosphates, $Al_2O_3$, $ZrO_2$, xerogels, bioactive glasses or funtionally bioactive or therapeutically active molecules, antigenes, antibiotics, desinfectants, radio opaque materials, organic acids such as maleic acids, polyacrylic acid, or the like; and b) evaporating the solvent which results in a highly porous polymer mass between the fibres, c) wetting the preform obtained in step b) in a monomer system, such as BISGMA-TEGDMA system, or in a multifunctional cross-linker (so-called dendrimer), said system optionally containing necessary chemical compounds required for subsequent polymerization of the monomers or dendrimers, where said monomers or dendrimers at least partly dissolve the highly porous thermoplastic mass between the fibres, d) pultruding the preform obtained in step c) through a mixture of a solvent and high molecular weight organic molecules in order to create a well bound IPN polymeric membrane for coverage of the fibres of the prepreg, e) optionally covering the mebrane with small particles of polymer, inert or bioactive fillers containing elements such as Si, Ca, P, Ba, Mg, K, Ti, F, oxides or other compounds of said elements, colour pigments, inert ceramics, hydroxy apatite (HA) or other Ca-phosphates, $Al_2O_3$, $ZrO_2$, xerogels, bioactive glasses or functionally bioactive or therapeutically active molecules, antigenes, antibiotics, desinfectants, radio opaque materials, and f) optionally packing the prepreg in a package containing metal foil bottom and optionally two layers of polymer sheet coverage; the closest to the prepreg being clear translucent sheet and the outermost sheet being a translucent sheet capable of avoiding initiation of light-polymerization by visible light in the case of light-polymerizable prepreg.

The prepreg thus obtained contains a polymer-monomer gel which binds the fibres sufficiently strongly together, and a thin polymeric high molecular weight thermoplastic membrane, which covers and protects the fibres of the prepreg. The high molecular weight molecules behave as fillers in the monomeric matrix, thus decreasing the required quantity of polymerizable monomers. The decreased quantity of monomers decreases in turn the polymerization contraction of the resin. The slightly sticky thermoplastic membrane also allows prepregs to have interstrand adhesion before polymerization.

The prepreg can be manufacturerd into desired form from continuous unidirectional fibres, a fibre weave, a fibre mat, fibre whiskers or any other form of fibres or filler particles. Mixtures of the various fibre forms can also be used.

Suitable fibres for the use in this invention are either inorganic or organic fibres. The choice of fibre depends highly on the technical field in which the fibre reinforced composite shall be used. Fibres already tested in dentistry include E-glass, S-glass, carbon/graphite, aramid and ultra-high-molecular-weight polyethylene fibres. It seems that glass fibres best fullfill the cosmetic and adhesive requirements for dental use. As other examples of suitable fibres can be mentioned fibres of bioactive glass and sol-gel derived silica fibres.

The monomers used in the first matrix component of the prepreg can be any kind of monomer or combination of monomers. Among preferable monomers can be mentioned e.g. 2,2-bis[4-(2-hydroxy-3-methacroyloxy)phenyl]propane (BISGMA), triethyleneglycoldimethacrylate (TEGDMA) or hydroxyethyldimethacrylate (HEMA).

The polymer used in the second matrix component of the prepreg is preferably a thermoplastic polymer in its dissolved form, such as PMMA. Thermoplactic polymers are preferred because they can dissolve into resins applied around the prepreg.

The polymer used in the third matrix component of the prepreg can be any thermoplastic polymer. The polymer most often used in dentistry and orthopedic surgery is polymethylmethacrylate (PMMA). Other suitable polymers are epsilon-caprolactone (PLA), epsilon-caprolactone, D- and L-lactide, PLA-, PGA-molecules, polyorthoesters, or other bioactive, biocompatible polymers.

During the fabrication process of the pregreg, the polymer chains of the preimpregnation polymer (third matrix component) (e.g. PMMA) are dissolved by the monomers (e.g. BISGMA-TEGDMA) or dendrimers of the first matrix component and they form a highly viscous gel containing high-molecular-weight molecules (PMMA) in monomeric phase (BISGMA-TEGDMA). The gel and the thin high-molecular-weight membrane (second matrix component) bind the fibres together and eliminate fraying of the fibres during handling. Either the monomeric phase or the high-molecular-weight molecule phase, or both, can contain chemical compounds required to initiate the polymerization reaction.

Figure 2:
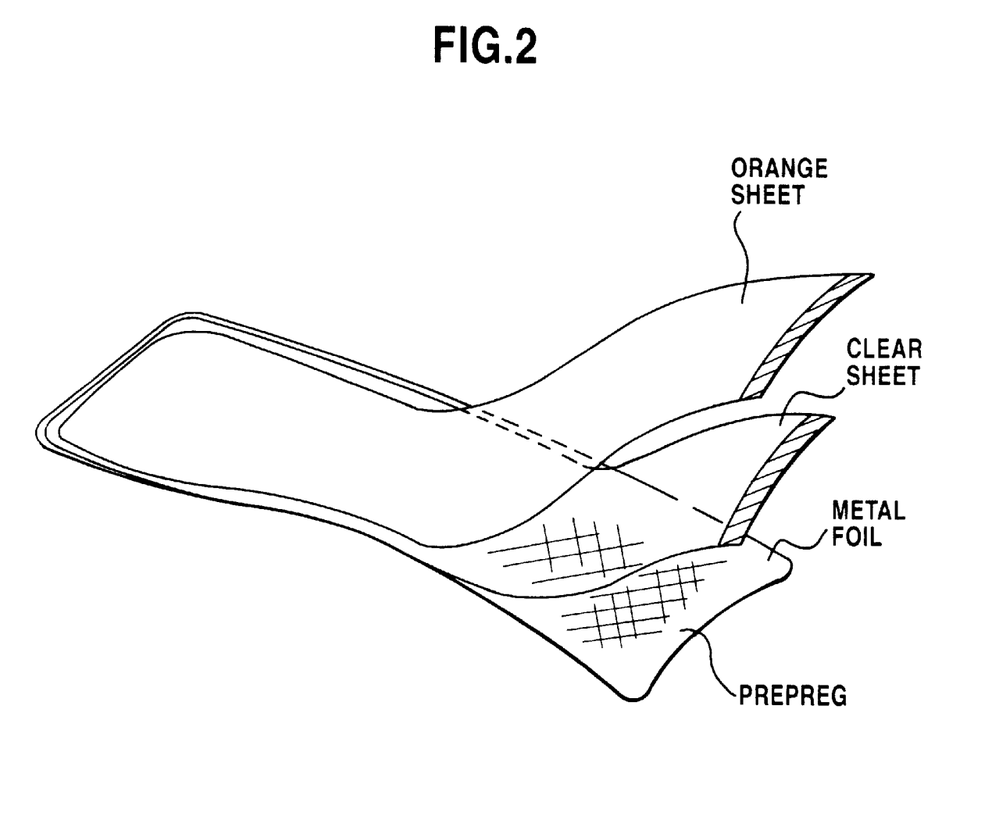
FIG. 2 shows a package of the prepreg.

The prepreg is preferably packaged into a package with metal foil bottom and optionally one or two layers plastic sheet coverage: the closest to the prepreg being clear translucent sheet and the second sheet being a translucent membrane capable of eliminating polymerization of the prepreg in the case of light-polymerizable prepreg by visible light. Preferably, the second sheet is orange coloured. The metal foil makes it possible to shape the prepreg into desired shape e.g on dental cast and the metal foil remains the shape until the the polymerization of the prepreg is completed. The plastic sheths elimates skin contact of the prepreg during shaping. Reference is made to FIG. 2.

After polymerization, the prepreg formed a fibre composite in which there are reinforcing fibers in multiphase polymer matrix. The multiphase polymer matrix contained the high-molecular-weight molecules of the thermoplastic polymer (e.g. PMMA), highly cross-linked copolymer system (e.g. BISGMA-TEGDMA or dendrimer) which are covered with a thin layer of thermoplastic membrane. The high-molecular-weight phases between the fibres are randomly orientated in the prepreg and regions of enriched high-molecular-weight molecules are bound to the cross-linked part of the polymer matrix with an IPN (interpenetrating polymer network)

The regions of enriched high-molecular-weight molecules between the fibres are in fact chains of the thermoplastic polymer (PMMA) (third matrix component) which are at least partly soluble in monomers or dendrimers. These PMMA chains in the cross-linked polymer matrix of the finally polymerized fibre composite and the thermoplastic membrane make it possible to obtain good bonding of any kind of resinous materials, such as those used in dental luting cements to the fibre composite. Good bonding is based on the formation of the IPN-layer between the thermoplastic chains in the polymer matrix or the thermoplastic membrane. Such bonding cannot be obtained with the highly cross-linked part of the polymer matrix (15).

The prepreg according to the this invention can be used in a great variety of fields:

1) In the orthopedic field can be mentioned plaster bandages replacing the traditional gypsum plasters. Plaster bandages made of the prepreg according to this invention are thin, light and durable. Appropriate colour pigments fillers, other fillers, therapeutical compounds or desinfectants improves the esthetical and medical qualities.

2) In case of bioactive ceramics or bioactive glasses or bioactive polymers are used, various supports enabling tissue contact with the support and tissue wound healing, can be constructed.

3) The prepreg can also be used to construct wound plasters, orthopedic support socks for the use around limbs, or for healing constructions for use in done or for dental surgery, periodontological or prosthetic use.

Furthermore, the prepreg according to this invention can also be used for many non-medical and non-dental purposes. It can be used for general technical purposes, e.g. as parts of instruments, as tools, devices, and materials and equipment which can be shaped freely for custom-made products, e.g. by hand or which can be shaped in molds with the influence of pressure or in a jig for mass production. Moreover, the prepreg can be used to repair voids, fails and fractures of various products.

The invention is illustrated by the following examples. In the examples the invention is explained in terms of its preferred embodiments and implications in dentistry even though the invention also has other medical and technical implications.

EXAMPLE 1

Preparation of the Prepreg From the Unimpregnated Fibres

The fibres were E-glass fibres (Ahlstrom, Karhula, Finland) with silane containing sizing. Fibre roving or woven roving, respectively, was pultruded through a liquid of monomers BISGMA and TEGDMA (first matrix component). The BISGMA-TEGDMA contained all chemicals required for photoinitiation of polymerization. Therefore, this and the following stages were carried out in a dark room or chamber. The subsequent pultrusion stage was made through liquid of solvent THF and dissolved PMMA molecules. This stage formed gel membrane of the prepreg (second matrix component) which bound the fibres together. The prepreg was then dried and cut to the desired pieces and packed into packages with aluminum foil bottom and two layers of polymer sheet coverage: the closest to the prepreg being clear translucent and the outermost being orange translucent sheet.

EXAMPLE 2

Preparation of the Prepreg From the Polymer Preimpregnated Fibres

A polymer preimpregnated (third matrix component) prepreg prepared according to Example 1 in WO 96/25911 was pultruded through a liquid of monomers of BISGMA-TEGDMA (first matrix component) which contained all of the chemicals required for photoinitiation of polymerization. The subsequent pultrusion stage was made through liquid of solvent THF and dissolved PMMA molecules (second matrix component) which formed the gel membrane. The packing was made as described in the Example 1.

EXAMPLE 3

Preparation of the Prepreg With Additional Bioglass Particle Surface

The fibre prepreg fabricated as described in Example 1 or 2 was pultruded through liquid of solvent THF and dissolved PMMA molecules to form the gel membrane for the prepreg. Before drying the gel, the prepreg was powder-coated with small particles of bioactive glass (particle size of 10–50 microns) which adhered to the surface of the prepreg during drying.

The following Examples describing the use of the prepreg refer to any of the prepregs described in the foregoing Examples 1 to 3.

EXAMPLE 4

The Use of the Prepreg in Fabrication of Periodontal Splint

The desired length of the prepreg was cut with scissors, the tooth enamel was etched with phosphoric acid and the normal dental bonding agents were used. The prepreg was then pressed againsts to the tooth by hand instruments with or without the aluminum foil package, and the prepreg was light-cured with a normal dental light-curing unit. The polymerized prepreg was bonded to the dental bonding agents which are dimethacrylate resins via IPN-layer formation of the thermoplastic phases of the prepreg and by radical polymerization of unreacted carbon—carbon bonds of the prepreg and dental bonding agent monomers. In the same way the prepreg could be used as periodontal splints which were placed into the cavities of teeth.

EXAMPLE 5

The Use of the Prepreg in Fabrication of Composite Crown or Bridge

The crown units of the bridge were made from the weave prepreg by pressing the prepreg over the abutment teeth of dental cast by transparent mould or with the help of the aluminum foil based package. The prepregs were light-cured through the transparent mould with a light-curing unit. The pontics of the bridge were made from continous unidirectional prepregs which were placed over the abutments and polymerized to the surface of weave prepregs on abutment teeth. The layer of prepregs bonded together by means of sticky nature of the prepregs and after polymerization the bond was based on radical polymerization and IPN layer formation. The fianally light-cured framework for the composite bridge was covered with normal tooth coloured composite resin which give the tooth appearance for the abutment and pontic teeth. The bridge was luted to the abutment teeth with normal resinuous luting cements and the bonding the cement to the composite frame of the bridge was based on the formation of IPN layer between the thermoplastic phase of the composite and the thermosetting luting cement as well as on the radical polymerization of the thermosetting luting cement monomers and unreacted double bonds of the polymerized prepreg.

EXAMPLE 6

The Use of the Prepreg in Fabrication of Resin-Bonded-Bridge

Figure 3:
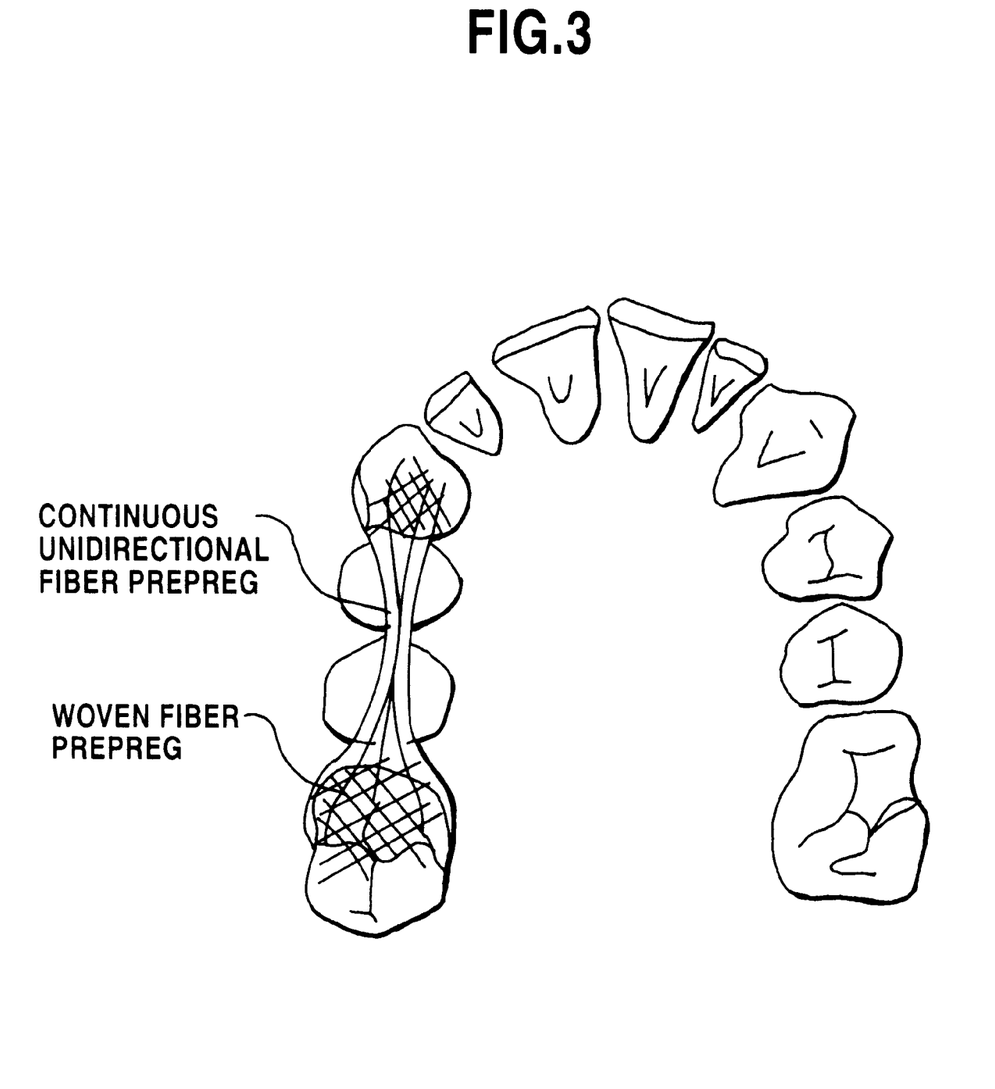
FIG. 3 shows a resin-bonded bridge based on the use of the prepreg.

The fabrication of a fibre composite resin-bonded-bridge (RBB) did not necessarily require any tooth preparation by grinding as a conventional bridge. The RBB was made on a primary dental cast by pressing an unidirectional prepreg against the abutment teeth surfaces and the prepreg was light-cured. The optional possibility to twist the prepreg around distal or mesial abutment increased the strength of the bridge considerably. The polymerized unidirectional prepreg was then rebased with a layer of weave prepreg and light-cured. Optionally, the frame of the prepreg was covered with another layer of weave prepreg. The pontic teeth of the RBB were made from tooth coloured dental composite resin. The RBB was luted to the etched enamel surface with normal dental luting cements. The bonding was based on the formation of IPN-layer and on radical polymerization. Reference is made to FIG. 3.

EXAMPLE 7

The Use of the Prepreg in Fabrication of a Root Canal Post

The continuous unidirectional fibre prepreg was pressed into the mould of the shape of the desired root canal post. The shape of the post could be either standardized or individual, i.e. the post could be finally cured to the predetermined form by the manufacturer of the post, or the post could be made from the prepreg direct to the prepared root canal in situ. The uncured prepreg was polymerized in the mould and removed from the mould. The composite post made from unidirectional fibre prepreg was luted into the tooth with resinuous dental luting cements. Good bonding between the post and cement was obtained by formation of a IPN layer between the thermoplastic phases of the post and luting cement.

Optionally the unidirectional fibre prepreg could be incorporated into the root canal of the tooth in prior to polymerization. The prepreg was cured with light and/or autopolymerization in situ.

EXAMPLE 8

The Use of the Prepreg as Dental Filling Material

The prepreg "bricks" made from randomly oriented fibres were packed into the cavity of tooth which had been treated with dental bonding agents. The high-molecular-weight molecule fractions of the prepreg made the material condensable and decreased the polymerization contraction of the filling material.

EXAMPLE 9

The Use of the Prepreg as Matrice for Dental Filling Material

The prepreg in thin woven form could be used as matrice for dental filling composite material. The prepreg matrice was such which was bonded permanently to the composite resin simultaneously with polymerization of the filling material, and thus, it formed a outer part of the filling. This kind of prepreg matrice eliminated the problem of formation of a gap between the restored tooth and the tooth beside it.

EXAMPLE 10

The Use of the Prepreg as Precision Attachment

Figure 4:
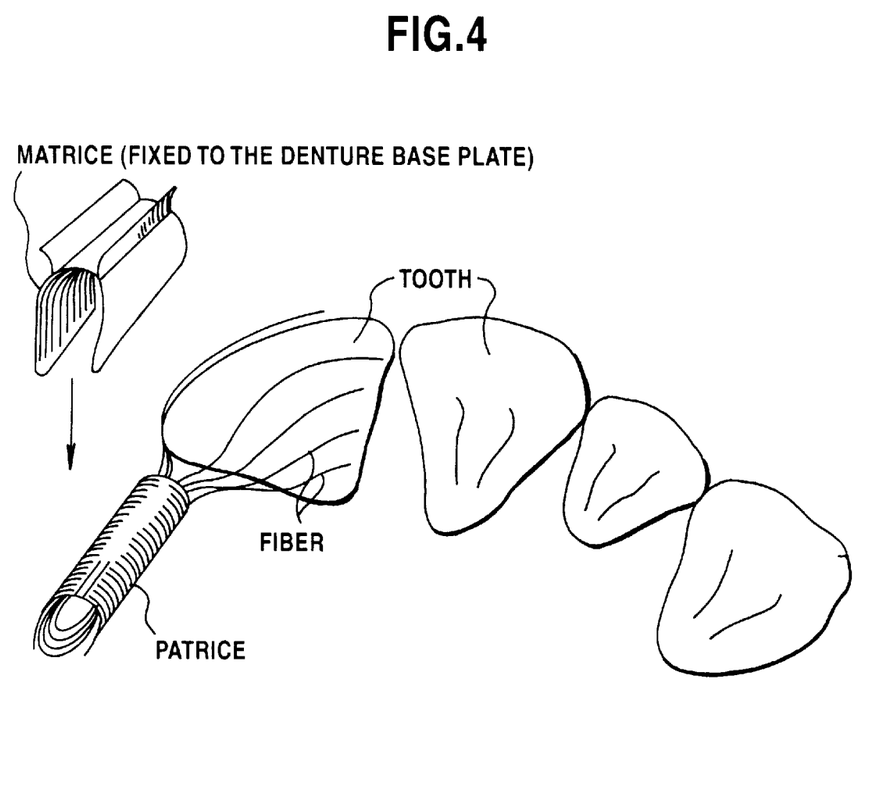
FIG. 4 shows a precision attachment based on the use of the prepreg.

The prepreg made from unidirectional or weave type of prepreg were used as resin bonded precision attachment for removable dentures. The unidirectional prepreg was twisted to cover the labial/buccal and palatal/lingual sides of the tooth. The loop part of the prepregs were covered with a gold plate or ceramic material in order to get a wear resistance surface. Alternatively, any kind of patrice or matrice part of the precision attachment could be used to replace the gold plate. The prepreg was polymerized and luted to the tooth surface with normal dental luting cements. The bonding was based on formation of an IPN layer. The removable denture was made over the dentition and patrice part of the precision attachment, i.e. made from the prepreg. The matrice part of the precision attachment was placed normally into the denture. Reference is made to FIG. 4.

EXAMPLE 11

The Use of Prepreg as Orthodontic Retainer

The prepreg made from unidirectional fibres or from woven fibres was luted to the etched enamel surface of the teeth after orthodontic treatment. Bonding to the enamel was made with normal dental adhesives and the prepreg was light-cured to the desired region of the dentition.

EXAMPLE 12

The Use of the Prepreg in Reparation of Polymeric Structures in Mouth

The prepreg, either made from continuous unidirectional fibres or fibre weave was placed onto the repair region of the dental construction in the mouth after the surface had been treated with any of the known techniques (e.g. acid etching, sandblasting, using dental adhesives) in order to get good bonding between the the prepreg and the repaired dental construction. Dental constructions which could be repaired with the prepreg were: tooth fillings, porcelain-fused-to-metal crowns and bridges, other type of bridges, ceramic crowns, precision attachments of removable dentures, and the like. After curing the prepreg, by light-polymerization, the surface of the prepreg was covered with tooth coloured polymeric material in order to improve the cosmetic qualities of the repaired region.

EXAMPLE 13

The Use of the Prepreg as Rebasing Material of Dental Constructions

Some dental constructions made in dental laboratory may have poor fit in situ. E.g. a crown, ceramic inlay or onlay filling or ceramic or polymeric veneer might be loose when their fitting on a tooth was tested. The weave prepreg was used to improve the fit of such constructions by placing a piece of the noncured prepreg between the construction and tooth when the construction was cemented onto the tooth. After curing of the luting cement and the prepreg, the luting cement was reinforced with the fibres of the prepreg. This also reduced the wear of the luting cement between the filling and the tooth.

EXAMPLE 14

The Use of the Prepreg as Preshaped Parts for Dental Constructions

The prepreg was preshaped approximately into the form of e.g. a core of the crown, pontic of a bridge, occlusal surface of a bridge, clasp of a denture by manufacturer of the prepreg. The dentist or dental technician used these gel-like noncured preshaped parts of the prepregs and positioned them on the dental cast or on the teeth, adjusted them into right shape and contour and allowed them to polymerize. The cured parts were then used in a conventional way to make final restoration or prosthetic construction. In the case of clasps of removable dentures or occlusal surfaces of teeth, some regions were prone to wear in the final product. This was eliminated by covering that particular surface of the preshaped prepreg with wear resistance particles like small tooth coloured ceramic brickets or some other type of layer of fillers.

EXAMPLE 15

The Use of the Prepreg as an Insert of the Dental Filling Material

The prepreg insert with the desired fibre direction considering the direction of occlusal forces in dentition was incorporated into the tooth cavity partly or totally filled with conventional dental filling material. After polymerization of the filling material and the prepreg, the fibres reinforced the polymeric filling. Optionally, the prepreg was polymerized into desired form in the tooth cavity, removed after which it was placed it into the cavity, which was filled with the filling material.

EXAMPLE 16

Repair of an Old Restoration Made From the Prepreg

The old restorative composite or other material was removed from the surface of the fibre-rich region, i.e. prepreg part of the construction. The removal exposed the structure of the prepreg which consisted of fibres and polymer phases of thermoplastic and thermosetting nature. The newly applied restorative composite on the surface of exposed fibre-rich surface was bonded by IPN mechanism to the thermoplastic phases of the fibre rich region and by radical polymerization mechanism to the remaining unreacted C—C double bonds of the other parts of the polymer matrix. These bonding mechanisms resulted in durable bond between restorative material and old fibre-reinforced composite.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

1. Watson R M, David D M. Follow up and maintainance of implant supported prostheses: a comparison of 20 complete mandibular overdentures and 20 complete mandibular fixed cantilever prostheses. Br Dent J 1996; 181: 321–327.

2. Darbar U R, Huggett R, Harrison A. Denture fracture—a survey. Br Dent J 1994; 176: 342–345.

3. Vallittu P K, Lassila V P, Lappalainen R. Evaluation of damage to removable dentures in two cities in Finland. Acta Odontol Scand 1993: 51: 363–369.

4. Pourdehimi B, Robinson H H, Schwartz P, Wagner H D. Fracture toughness of kevlar 29/polymethyl methacrylate composite materials for surgical implantations. Ann Biomed Eng 1986; 14: 277–294.

5. Pilliar R M, Blackwell R, Macnab I, Cameron H U. Carbon fiber-reinforced bone cement in orthopedic surgery. J Biomed Mater Res 1976; 10: 893–906.

6. Vallittu P, A polymer—fibre prepreg, a method for the preparation thereof as well as the use of said prepreg. International Patent Appl. Publ. No. WO 96/25911.

7. Ruyter I E, Svendsen S A. Flexural properties of denture base polymers. J Prosthet Dent 1980: 43; 95–104.

8. Vallittu P K, Glass fiber reinforcement in repaired acrylic resin removable dnetures: preliminary results of a clinical study. Quintessence Int 1997; 28: 39–44.

9. Ruyter I E, Types of resin-based inlay materials and their properties. Int Dent J 1992; 42: 139–144.

10. Altieri J V, Burstone C J, Goldberg A J, Patel A P. Longitudinal clinical evaluation of fiber-reinforced composite fixed partial dentures: A pilot study. J Prosthet Dent 1994; 71: 16–22.

11. Pröbster B, Henrich G M. 11-year follow-up study of resin-bonded fixed partial dentures. Int J Prosthodont 1997; 10: 259–268.

12. King P A, Setchell D J. An invirto evaluation of a prototype CFRC prefabricated post developed for the restoration of pulpless teeth. J Oral Rehabil 1990; 17: 599–609.

13. Purton D G, Payne J A. Comparison of carbon fiber and stainless steel root canal posts. Quintessence Int 1996; 27: 93–97.

14. King P A, Setchell D J. 7 year clinical evaluation of a prototype CFRC endodontic post. J Dent Res 1997; 76: 293. (Abstract)

15. Sperling L H. Interpenetrating polymer networks and related properties. Plenum Press, New York 1981.

16. U.S. Pat. No. 4,264,655: Encapsulated impregnated rovings, 1981.

17. U.S. Pat. No. 5,597,631: Prepreg, composite molding body, and method of manufacture of the composite molded body. 1997.

What is claimed is:

1. A shapable prepreg comprising fibres and a polymeric matrix, characterized in that the polymeric matrix is a multiphase matrix comprising
   a first matrix component consisting of a monomer or a dendrimer, and
   a second matrix component consisting of high molecular weight organic molecules, said second matrix component forming a sticky membrane of the prepreg with an interpenetrating polymer network (IPN) bonding to the first matrix component.

2. The prepreg according to claim 1, characterized in that it further comprises a third matrix component consisting of high molecular weight organic molecules, said third matrix component being distributed between the fibres.

3. The prepreg according to claim 1, characterized in that the prepreg is able to bond to surrounding resin materials with an IPN mechanism and radical polymerization.

4. The prepreg according to claim 2, characterized in that the first matrix component, which is a monomer or a dendrimer, and the third matrix components form a gel, and that the prepreg contains ingredients necessary to initiate the polymerization at a desired point of time.

5. The prepreg according to claim 1, characterized in that the second matrix component and the third matrix component both consists of polymethylmethacrylate (PMMA).

6. The prepreg according to claim 4, characterized in that the monomer is 2,2-bis[4-(2-hydroxy-3-methacroyloxy) phenyl]propane (BISGMA), triethyleneglycoldimethacrylate (TEGDMA) or a dendrimer.

7. The prepreg according to claim 1, characterized in that it contains further additives.

8. The prepreg according to claim 7, characterized in that the additives are different inert or bioactive fillers containing elements such as Si, Ca, P, Ba, Mg, K, Na, Ti, F, oxides or other coumpounds of said elements, colour pigments, inert ceramics; hydroxyapatite (HA) or other Ca phosphates, $Al_2O_3$, $ZrO_2$, xerogels, bioactive glasses or functionally bioactive or therapeutically active molecules, antigens, antibiotics, desinfectants, radio opaque materials, organic acids such as maleic acid, polyacrylic acid, or the like.

9. The prepreg according to claim 1, characterized in that the thermoplastic components of the prepreg allow formation of an interpenetrating polymer network (IPN) layer for bonding any kind of resinous materials to the surface of the finally cured composite made from the prepreg and the resinous material.

10. The prepreg according to the claim 1, characterized in that the fibres are in the form of yarn, roving, woven roving, continuous fibre mat, shopped strand mat, short fibres, a whisker or particle formed, or a mixture of the aforementioned.

11. The prepreg according to claim 1, characterized in that the fibres are inorganic fibres, such as glass or carbon/graphite fibres, or organic fibres such as aramid or ultra-high-molecular-weight polyethylene fibres, or any kind or reinforcing fibres of fillers or their combinations.

12. A prepreg comprising fibers and a polymer distributed between the fibres, characterized in that the polymer is epsilon-caprolactone/PLA, epsilon-caprolactone, D- and L-lactide, PLA-, PGA-molecules, polyorthoesters, or an other bioactive, biocompatible polymers having molecular weight in the range 5,000 to 400,000.

13. A prepreg comprising fibers and a polymer distributed between fibres, characterized in that the between the fibres are further distributed additives such as Si, Ca, P, Ba, Mg, K, Na, Ti, F, oxides or other coumpounds of said elements, colour pigments, inert ceramics; hydroxyapatite (HA) or other Ca phosphates, $Al_2O_3$, $ZrO_2$, xerogels, bioactive glasses or functionally bioactive or therapeutically active molecules, antigens, antibiotics, desinfectants, radio opaque materials, organic acids such as maleic acid, polyacrylic acid, or the like.

14. A process for the preparation of the prepreg claimed in claim 1, characterized in that fibres are wetted in a monomer or a dendrimer, and that the product so obtained optionally is further wetted in a solution of high molecular weight organic molecules.

15. A process according to claim 14, characterized that the the membrane is a thermoplastic material, optionally covered with one or more additives such as Si, Ca, P, Ba, Mg, K, Na, Ti, F, oxides or other coumpounds of said elements, colour pigments, inert ceramics; hydroxyapatite (HA) or other Ca phosphates, $Al_2O_3$, $ZrO_2$, xerogels, bioactive glasses or functionally bioactive or therapeutically active molecules, antigens, antibiotics, desinfectants, radio opaque materials, organic acids such as maleic acid, polyacrylic acid, or the like.

16. The process according to claim 14, characterized in that a third matrix component consisting of high molecular weight organic molecules has been distributed between the fibres before the fibres are wetted with the monomer or dendrimer.

17. A package of the prepreg according to claim 1, characterized in that it comprises the prepreg surrounded by a metal foil bottom and one or two layers of plastic sheet coverage, the closest sheet to the prepreg being a clear translucent sheet and the outermost sheet being a translucent sheet, treated so as to not essentially pass the light for curing.

18. A fibre-reinforced composite incorporating the prepreg according to the claim 1.

19. The composite according to the claim 18 machined into one or more desired blocks or into a desired form.

20. The composite according to claim 18 for use in medical or dental constructions such as prosthodontics, restorative dentistry, orthodontics, orthopedic appliances and cements; removable denture frameworks or precision attachments, clasps, dental bridges, resin-bonded-bridges, root canal posts, cores, periodontal splints, orthodontic retainers, crowns, fillings, mouth guards, matrices and inserts for dental filling material and the like.

21. The composite according to claim 18 for technical use as parts of instruments, as tools, devices, and materials and equipments which can be shaped freely for custom-made purposes or used in mass production.

* * * * *